United States Patent [19]

Garcia et al.

[11] Patent Number: 4,475,889
[45] Date of Patent: Oct. 9, 1984

[54] SPEED-INCREASING DEVICE FOR A DENTAL HANDPIECE

[76] Inventors: Philippe Garcia, 5, rue de la Mouillere, 25 000 Besancon; Roger Gaillard, Busy 25320, Montferrand Le Chateau, both of France

[21] Appl. No.: 442,626

[22] Filed: Nov. 18, 1982

[30] Foreign Application Priority Data

Nov. 23, 1981 [FR] France ................................. 81 22012

[51] Int. Cl.³ ................................................ A61C 1/02
[52] U.S. Cl. .................................. 433/103; 433/105; 433/114; 408/124
[58] Field of Search ............... 433/103, 105, 114, 126, 433/131, 133; 74/393; 408/124

[56] References Cited

U.S. PATENT DOCUMENTS

| 269.611 | 12/1882 | Acheson | 433/105 |
| 937,126 | 10/1909 | Wentworth et al. | 433/103 |
| 950,759 | 3/1910 | Weiner | 433/131 |
| 1,945,053 | 1/1934 | Lundin | 408/124 |
| 2,138,945 | 12/1938 | Stolte et al. | 433/133 |
| 2,228,622 | 1/1941 | Emrick | 408/124 |
| 2,377,659 | 6/1945 | Zeichner | 408/124 |
| 3,324,553 | 6/1967 | Borden | 433/126 |

FOREIGN PATENT DOCUMENTS

| 711634 | 10/1941 | Fed. Rep. of Germany | 433/133 |
| 1052653 | 1/1954 | France | 433/114 |
| 1410432 | 10/1975 | United Kingdom | 433/105 |

Primary Examiner—John J. Wilson
Attorney, Agent, or Firm—Robert E. Burns; Emmanuel J. Lobato; Bruce L. Adams

[57] ABSTRACT

An angle-drive head of a dental handpiece with the housing thereof removable. A speed-increasing pinion is provided for meshing with a drive pinion of the angle-drive. A shaft connected to the pinion extends axially in the head and has a speed-increasing pinion for developing a greater speed. A speed-increasing device removably coupled to the head has a third speed-increasing pinion and a fourth pinion is coupled thereto. A tool-receiving jaw is provided in the device for coupling to the fourth speed-increasing pinion for being rotationally driven therefrom.

3 Claims, 6 Drawing Figures

FIG. I
(PRIOR ART)

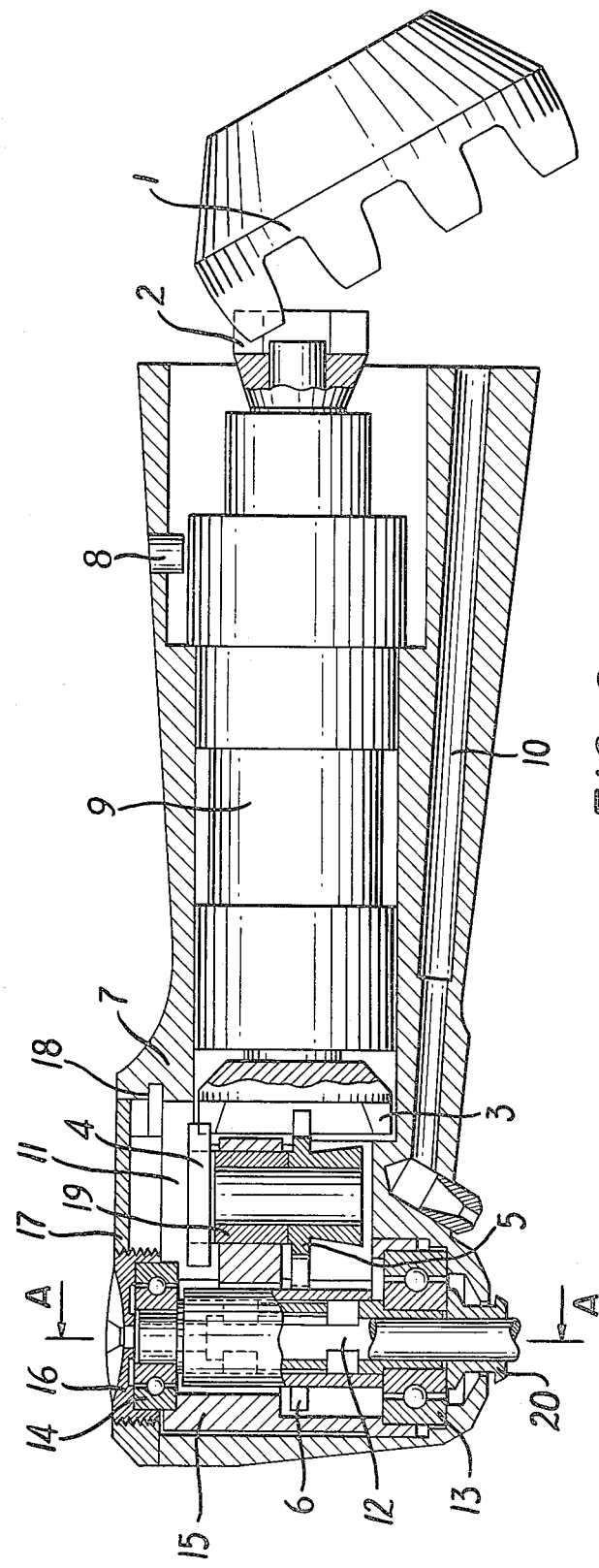
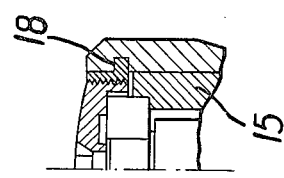
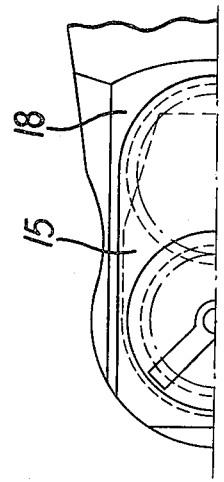
FIG. 2
FIG. 3
FIG. 4

SPEED-INCREASING DEVICE FOR A DENTAL HANDPIECE

BACKGROUND OF THE INVENTION

The subject of the present invention is a speed-increasing device for the rotary driving mechanism of a tool fixed in the head of an angle-drive used in dentistry, of the type which consists of a shaft which is driven directly by the driving shaft on which the angle-drive is arranged, and the said shaft meshes at its end with a first pinion of an inclined shaft, the said inclined shaft carrying a second pinion at its other end.

Speed-increasing angle-drives of this type have been known for a long time. In systems of the prior art, the said second pinion of the inclined shaft meshes directly with the pinion on the head spindle of the angle-drive.

In these devices, the pinion on the shaft driven by the motor turns at about 40,000 revolutions per minute.

The inclined shaft turns at about 80,000 revolutions per minute which gives the tool a speed of rotation of 120,000 revolutions per minute.

It is now desired to achieve higher head speeds, of the order of 160,000 revolutions per minute.

With known devices, this may only be obtained with an inclined shaft turning at 120,000 revolutions per minute. This is excessive for the moving parts concerned, and results in unbalance and vibration.

SUMMARY OF THE INVENTION

The aim of the present invention is therefore to enable the speed in the head to be increased to a higher rate, while reducing or limiting the speed of the inclined shaft of the angle-drive.

According to the invention, this result is obtained with a speed-increasing device for the rotary driving mechanism of a tool fixed in the head of an angle-drive used in dentistry, of the type which consists of a shaft which is driven directly by the driving shaft on which the angle-drive is arranged, and the shaft meshes at its end with a first pinion of an inclined shaft, the inclined shaft carrying a second pinion at its other end, is characterised in that the second pinion meshes with a first pinion of a speed increaser. A second pinion of the speed increaser meshes with the pinion on the head spindle of the instrument, and the speed increaser shaft is arranged parallel to the head spindle, and thus perpendicular to the inclined shaft of the angle-drive.

By this modification to the kinematic chain, speeds of the order of 160,000 revolutions per minute are obtained at the head of the angle-drive.

BRIEF DESCRIPTION OF THE DRAWINGS

The invention will be better understood with the aid of the following description and with reference to the accompanying drawings, in which:

FIG. 2 is a longitudinal section view of an angle-drive used in dentistry, incorporating a speed-increasing device according to the invention;

FIG. 3 is a fragmentary section along A—A in FIG. 2;

FIG. 4 is a plan view in half-section of FIG. 2;

DESCRIPTION OF THE PREFERRED EMBODIMENTS

Figure 1:
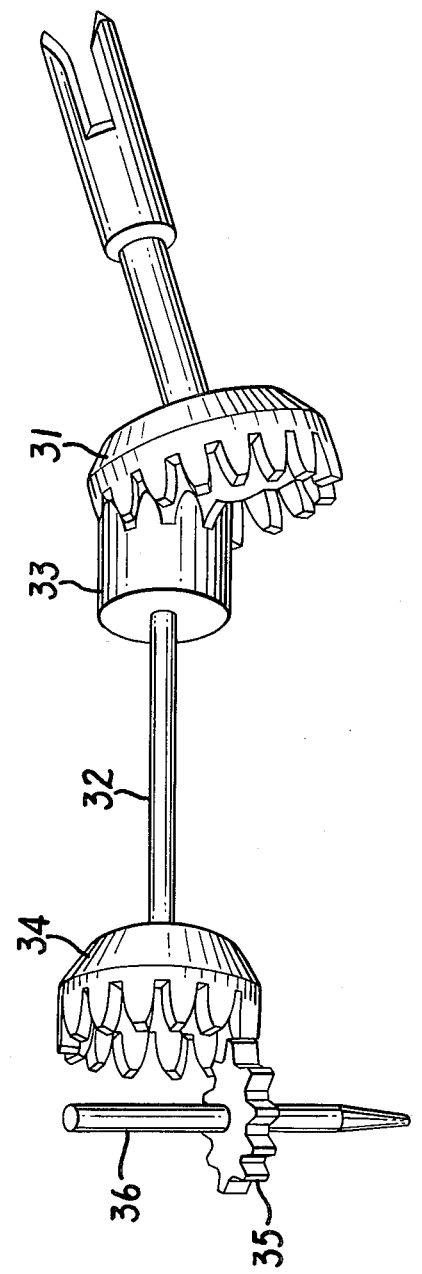
FIG. 1 is a perspective view illustrating diagrammatically a speed-increasing device of the prior art.

To begin with, the operation of a speed-increasing device of the prior art will be described with reference to FIG. 1.

If the driving pinion 31 of 18 teeth turns at 40,000 revolutions per minute, the inclined shaft 32 with a pinion 33 of 9 teeth will turn at 80,000 revolutions per minute.

The second pinion 35, of 14 teeth, on the inclined shaft meshes with the pinion of the head spindle 36 (10 teeth) which produces a rotational speed for the tool of: $40,000 \times 18/9 \times 14/10 = 112,000$.

Reference will now be made to FIG. 2.

In an angle-drive of the type which is in itself known, the shaft of the angle-drive which is driven directly from the end of the driving shaft carries a pinion (1) at the elbow, which drives a first pinion (2) on the inclined shaft (9).

The inclined shaft (9) carries at its other end a second pinion (3) which drives the first pinion (4) of a speed-increasing device (11) which will be described in detail at a later stage.

A second pinion (5) of the said speed-increasing device finally drives a pinion (6) in rotation on the head spindle and hence the tool which is held in the angle-drive head.

The following calculation may now be made, to be compared with the kinematic chain of FIG. 1. Taking pinions with the following characteristics:

Pinion (1): 20 teeth
Pinion (2): 9 teeth
Pinion (3): 14 teeth
Pinion (4): 10 teeth
Pinion (5): 13 teeth
Pinion (6): 10 teeth together with the same motor speed of 40,000 revolutions per minute, a speed at the head of the angle-drive of: $40,000 \times 20/9 \times 14/10 \times 13/10 = 161,000$ revolutions per minute will be obtained.

This is obtained with a rotational speed of the inclined shaft of 88,000 revolutions per minute, that is to say a speed essentially identical to that of the example shown in FIG. 1. The desired result is thus fully achieved.

A detailed description follows of the construction of the speed-increasing device according to the invention.

A body (7) of an angle drive head is similar, for example, to those of the angle-drives described in French Patent Applications Nos. 77-04027 and 78-37117 in the name of the Applicant Company (without limitation).

The body (7) of an angle-drive head is attached to the handle of the angle-drive (not shown), in a manner in itself known, by two pins (8) which engage in bayonet slots in the handle.

In a manner which is also conventional, the inclined shaft (9) of the angle-drive head is retained in a sleeve which is itself a light press-fit in the body of the head.

One or more passages (10) are arranged in the body (7) of the angle-drive head to convey spray fluids for drilling and/or for cooling the head.

The drill supported by the angle-drive head is held, for example, by friction in a jaw (12) similar to that which is the subject of French Pat. No. 1,255,386 in the name of the Applicant Company, and to which particular reference is made. This jaw turns, in a manner in itself known, in two ball journal bearings (13) and (14). It will also be understood that other constructions may be considered for this region without departing from the framework of the invention.

The bearing (13) is held in the head body near the bottom (with reference to FIG. 2). On its other face, the outer race of the bearing is retained by a support housing (15), whose upper part is itself clamped by the outer race of the bearing (14) and a screw (16). The screw (16) is screwed into a cap (17) which is fixed in the body (7) by means of a slide arrangement (18).

The shape of the support housing (15) is such that it may be removed from the head through the upper opening in the latter (see the construction shown in in dotted lines in FIG. 4).

The function of the support housing (15) is twofold:
to position the head bearings (13) and (14) in the angle-drive head,
to support the actual speed-increasing device (11).

The speed-increasing device (11) consists of a plane bearing (19) in which the abovementioned pinions (4) and (5) turn. This bearing (19) is supported by the housing (15). The pinions (4) and (5) are pressed one into the other, the pinion (5) being provided with a conical portion which enables it to be held for extraction when necessary.

Finally, the pinion (6) of the head spindle is pressed onto one end of the jaw (12) and guided by the other end, the two shells in the middle part of the jaw remaining free.

The penetration of water into the head of the angle-drive is prevented, with advantage, by a seal (20).

It will be understood that the essence of the invention lies in the presence and the construction of the speed-increasing device, independently of the arbitrary constructions of the head and of the body of the angle-drive.

Figure 5:
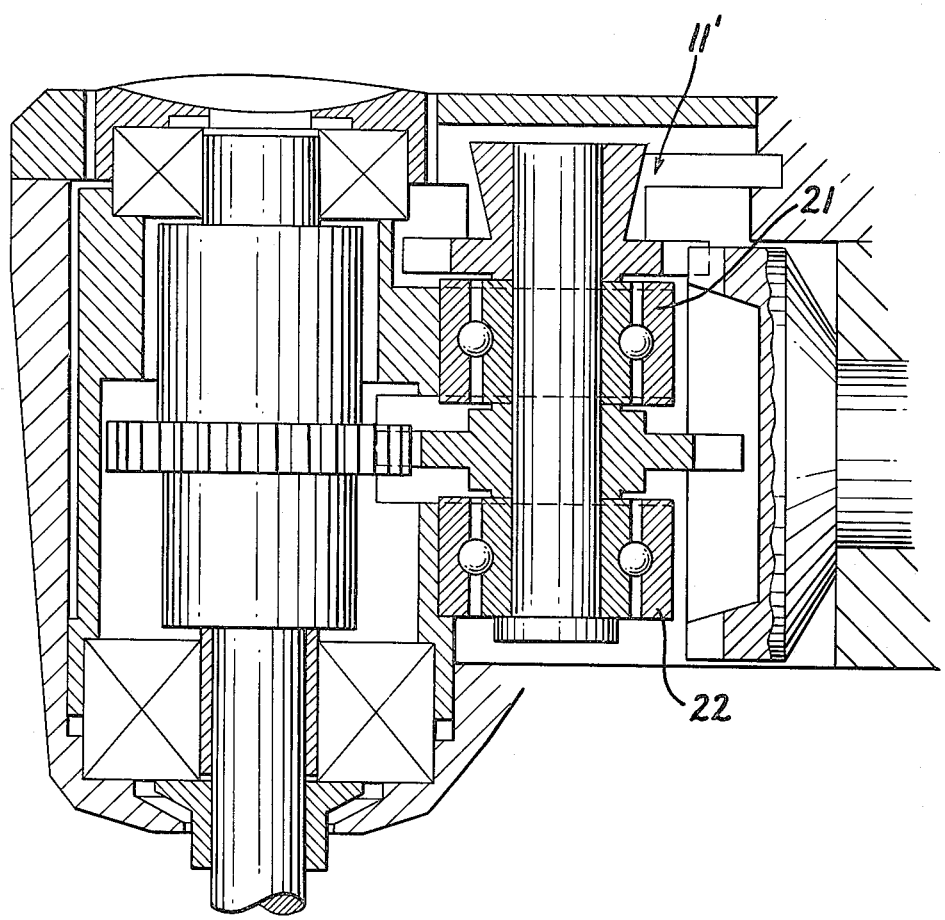
FIG. 5 is a longitudinal section view of a variation of FIG. 2.
Figure 6:
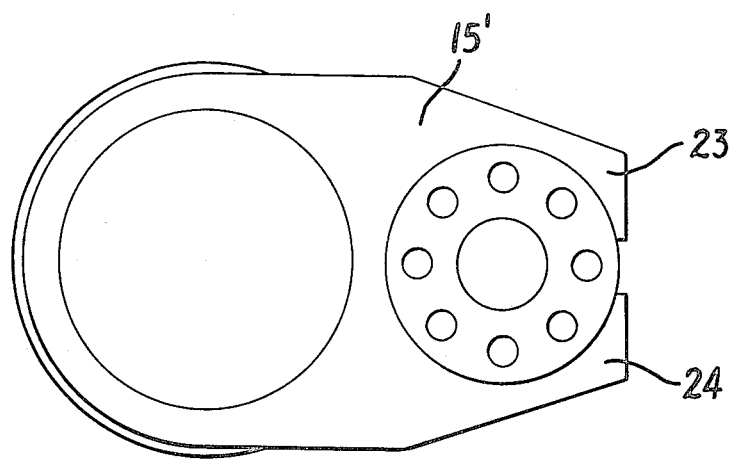
FIG. 6 is a fragmentary plan view of the device in FIG. 5.

Thus FIG. 5 shows a variation of the embodiment of the construction of the speed-increasing device, the functions remaining identical.

In this embodiment, the speed-increasing device (11') is no longer mounted in a plane bearing, but with two ball journal bearings (21, 22). The bearings are held in the region of their outer races by the elastic lugs (23, 24) of the support housing (15').

We claim:

1. In combination an angle-drive head of a dental handpiece having a housing removably attachable to the angle-drive and having a speed-increasing first pinion for meshing with a drive pinion of the angle-drive, a shaft connected to the first-mentioned pinion extending axially in the head and having a speed-increasing second pinion connected to said shaft at an opposite end thereof for developing an output speed greater than said first pinion, a speed increasing device removably coupled to said head comprising a support housing, a speed-increasing third-pinion in said support housing for developing a speed greater than said second pinion and having an axis of rotation normal to the longitudinal axis of said shaft and normal to the axis of rotation of the first and second pinions, a speed-increasing fourth pinion coupled to the same axis of rotation as said third pinion, a dental tool-receiving jaw in said support housing having an axis of rotation parallel to the axis of rotation of speed-increasing third and fourth pinions, and means for coupling the dental tool-receiving jaw to said speed-increasing fourth pinion for being rotationally driven therefrom.

2. The combination according to claim 1, including means for removably securing said support housing and speed-increasing device therein to said angle-drive head.

3. The combination according to claim 1, in which the speed-increasing third and fourth pinions are directly coupled.

* * * * *